US011944748B2

(12) United States Patent
McCain et al.

(10) Patent No.: US 11,944,748 B2
(45) Date of Patent: Apr. 2, 2024

(54) ACOUSTIC DOSE METER

(71) Applicants: Aisha McCain, Pittsburg, CA (US); Annemarie Sheets, Pittsburg, CA (US)

(72) Inventors: Aisha McCain, Pittsburg, CA (US); Annemarie Sheets, Pittsburg, CA (US)

(73) Assignee: Create To Overcome LLC, Pittsburg, CA (US)

( * ) Notice: Subject to any disclaimer, the term of this patent is extended or adjusted under 35 U.S.C. 154(b) by 0 days.

(21) Appl. No.: 17/883,939

(22) Filed: Aug. 9, 2022

(65) Prior Publication Data
US 2023/0037479 A1 Feb. 9, 2023

Related U.S. Application Data

(60) Provisional application No. 63/231,215, filed on Aug. 9, 2021.

(51) Int. Cl.
*A61M 15/00* (2006.01)

(52) U.S. Cl.
CPC ...... *A61M 15/008* (2014.02); *A61M 15/0068* (2014.02); *A61M 15/009* (2013.01); *A61M 2205/3375* (2013.01); *A61M 2205/3553* (2013.01); *A61M 2205/3584* (2013.01); *A61M 2205/502* (2013.01); *A61M 2205/583* (2013.01); *A61M 2205/8206* (2013.01); *A61M 2205/8262* (2013.01)

(58) Field of Classification Search
CPC ................ A61M 15/008; A61M 15/0068
See application file for complete search history.

(56) References Cited

U.S. PATENT DOCUMENTS

| 5,544,647 | A | * | 8/1996 | Jewett | A61M 15/008 |
| | | | | | 128/200.23 |
| 5,809,997 | A | * | 9/1998 | Wolf | A61M 15/0005 |
| | | | | | 128/200.23 |
| 2005/0076904 | A1 | * | 4/2005 | Jones | A61M 15/009 |
| | | | | | 128/200.23 |
| 2016/0051776 | A1 | * | 2/2016 | Von Hollen | A61M 15/009 |
| | | | | | 128/203.14 |
| 2016/0325057 | A1 | * | 11/2016 | Morrison | A61M 15/0071 |
| 2017/0182258 | A1 | * | 6/2017 | Michael | A61M 5/31568 |
| 2018/0154086 | A1 | * | 6/2018 | Toporek | A61M 5/31585 |
| 2020/0114087 | A1 | * | 4/2020 | Bauer | A61M 5/31568 |

* cited by examiner

*Primary Examiner* — Courtney B Fredrickson
(74) *Attorney, Agent, or Firm* — Cynthia S. Lamon; Lamon Patent Services

(57) ABSTRACT

An acoustic dose meter is provided comprising a housing, and a cylindrical seat for staging a pressurized medicine canister. The housing includes at least one compartment for housing electronics and passageways for connecting electronics for power and data communication. A microprocessor including a transient memory containing machine instruction is also included. Additionally, a power source connected to the microprocessor, a power switch connected to the microprocessor and the power source for booting the microprocessor are added. At least one visual display device connected to the microprocessor for displaying available doses is provided. A first set of acoustic sensors connected to the microprocessor and adapted as acoustic sound generators and a second set of acoustic sensors connected to the microprocessor and adapted as acoustic soundwave recorders are implemented to detect and analyze frequencies enabling determining of dosing count availability.

20 Claims, 3 Drawing Sheets

ACOUSTIC DOSE METER

CROSS-REFERENCE TO RELATED DOCUMENTS

The present invention claims priority to a U.S. provisional patent application Ser. No. 63/231,215 entitled Acoustic Dose Availability Meter filed on Aug. 9, 2021, disclosure of which is incorporated herein at least by reference.

BACKGROUND OF THE INVENTION

1. Field of the Invention

The present invention is in the field of medical devices, more particularly metered dose inhalers (MDIs) and pertains particularly to methods and apparatus for determining the dose availability in a pressurized MDI medicine canister.

2. Discussion of the State of the Art

A metered dose inhaler (MDI) is a well-known medical device that is adapted to position a pressurized canister of medicine for actuated aerosol dispense of a metered dose of the pressurized medicine into a patient's lungs. Medications for breathing problems, such as asthma and chronic obstructive pulmonary disease (COPD), are commonly delivered directly to the lungs from an MDI. These medications include albuterol and steroids, among others. A meter dose inhaler (MDI) is commonly termed an inhaler in the art. Most inhaler devices are MDI devices. For example, the drug albuterol delivered by a MDI is the fastest way to reverse an asthma attack. The medicine allows the muscles around branches of the lungs to relax. Asthma is a common, chronic respiratory disease that affects approximately 26 million people in the US. It is the most common chronic disease in childhood, affecting an estimated 7 million children. The estimated of lost work and school time from asthma is approximately 100 million days of restricted activity. Approximately 500,000 annual hospitalizations (40.6% in individuals aged 18 y or younger) are due to asthma. Each year, an estimated 1.7 million people (47.8% of them aged 18 years or younger) require treatment in an emergency department. For 2010, the annual expenditures for health and lost productivity due to asthma was projected to be $20.7 billion.

A medicine canister for an MDI may be a multiple dose canister meaning that a patient may inhale a number of metered doses from the single MDI canister. MDI devices may vary in physical architectures and medicine dispensary metrics. In some devices, mechanical plastic gears and scrolling tape have be incorporated as a mechanism to enable a patient to discern the availability of available doses left in the canister. In essence by counting the number of available doses left in the canister where each actuation of the canister delivers a measured dose of the pressurized medicine.

In some other MDI devices, an electronic sensor has been provided and adapted to count the discharged volume of medicine through a discharge stem at one end of the canister at the instant the actuation and discharge occurs during normal use. However, this is not common in the known art. The FDA will only allow dose counters that are specific to the type of canister and the type of medication delivered. This is due to the disparity in MDIs, recommended dosages, patient behaviors, and biochemical properties of a variety of medications available to MDI patients. In current art, there are no universal methods or apparatus for quantifying available dosages left in an MDI canister across disparate MDI devices. When a user experiences a major health emergency, it is critical that the user be aware of how many doses are available in their MDI device canisters. Picking up an MDI device without a viable dose left in a life-threatening emergency could be fatal. Therefore, what is clearly needed is a method and apparatus for evaluating and discerning how many doses in an MDI canister are available to a patient and that provides the availability information to the patient in a universal manner across disparate MDI device types.

BRIEF SUMMARY OF THE INVENTION

According to an embodiment of the present invention, an acoustic dose meter is provided and consists of a housing including a cylindrical seat for staging a pressurized medicine canister for testing, the housing including at least one compartment for housing electronics and passageways for connecting electronics for power and data communication, a microprocessor including a transient memory containing machine instruction, a power source connected to the microprocessor, a power switch connected to the microprocessor and the power source for booting the microprocessor, at least one visual display device connected to the microprocessor, a first set of acoustic sensors supported by the housing the sensors connected to the microprocessor and adapted as acoustic sound generators, and a second set of acoustic sensors supported by the housing, the sensors connected to the microprocessor and adapted as acoustic soundwave recorders. In one embodiment the sensors may be piezo-electric acoustic sensors.

In one embodiment, the power source is a rechargeable battery. In one embodiment, the acoustic dose meter further includes a micro universal serial bus charging port connected to the microprocessor. In a preferred embodiment, the medicine canister seat has a diameter larger than the outside diameter of the medicine canister and a length equal to or greater than the length of the medicine canister, and a centered bore disposed at the bottom to accommodate an actuator of the medicine canister. In this embodiment, the canister seat is a counter bored feature substantially centered in the housing.

In one embodiment, the first and second sets of acoustic sensors are arrayed linearly and equally spaced apart, the first and second sets disposed on opposite sides of the canister seat and aligned, the first set emitting soundwaves of a known frequency, the second set detecting the soundwaves at the same or different frequency. In the embodiment using a battery as a power source, the acoustic dose meter further includes a light emitting diode adapted to notify of successful charge state of the battery.

In one embodiment, the acoustic dose meter further includes a wireless communication chip connected to the microprocessor enabling data transfer from the acoustic dose meter to another wireless appliance. In a variation to this embodiment, the wireless communication chip is a Bluetooth™ communication chip. In one embodiment, second set of acoustic sensors communicate detected frequency values to the microprocessor over a data line or trace. In one embodiment, the visual display device is a liquid crystal display device controlled at the microprocessor. In one embodiment, the machine instructions include one or more instructions for quantifying detected soundwave frequencies, differentiating the frequencies detected from the original frequencies emitted, and deriving available dose information based on the differences in frequencies and the original capacity of the medicine canister.

In a preferred embodiment, the available dose information is displayed on the liquid crystal display device. Also in a preferred embodiment, the dose information displayed is the number of metered doses still available in the medicine canister. In the embodiment using wireless communication, the other wireless appliance in communication with the dose meter is a cellular phone running a thin client application adapted as a user interface to the acoustic dose meter. In a variation of this embodiment, the cellular phone has connection to a data network supporting at least one medical provider portal and at least one emergency services portal. In another variation to the embodiment, a wireless notification is communicated from the dose meter to the cellular phone the notification including the available dose information for the medicine canister.

In one embodiment, the microprocessor and rechargeable battery are disposed within the at least one compartment and are accessible through a compartment door. In one embodiment, the first and second sets of acoustic sensors are embedded into the housing material inside the canister seat in a manner that does not obstruct the interior space of the canister seat. In one embodiment, the medicine canister is one of a metered dose inhaler device.

DETAILED DESCRIPTION OF THE INVENTION

In various embodiments described in enabling detail herein, the inventor provides a unique apparatus adapted to monitor capacity within a pressurized medicine canister and report or otherwise make available current dose availability along with other data to a patient and to agents of the patient. For the purposes of this specification, an agent of the patient shall mean any individual or group acting on behalf of the patient. A goal of the present invention is to provide a meter device adapted to test and calculate how many metered doses are left in a multiple dose medicine canister for a metered dose inhaler (MDI). Another goal of the present invention is to reduce or eliminate manual tasking associated with patient management of MDI use and record keeping. The present invention is described using the following examples, which may describe more than one relevant embodiment falling within the scope of the invention.

Figure 1A:
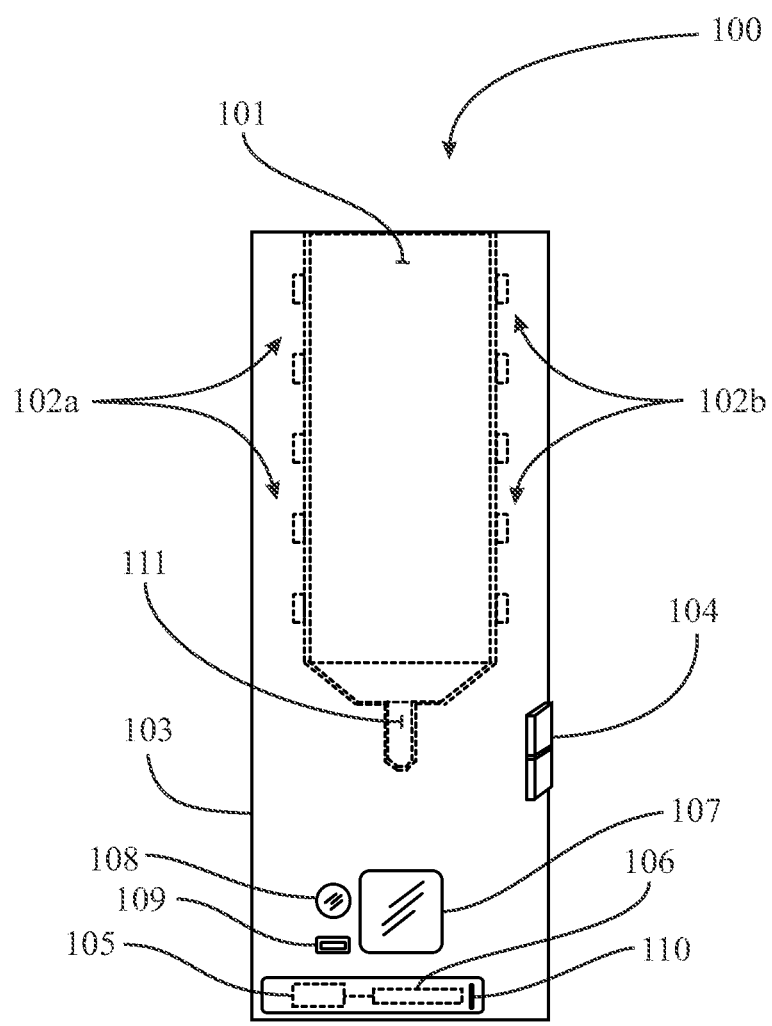
FIG. 1A is an elevation view of a acoustic dose meter according to an embodiment of the present invention.

FIG. 1A is an elevation view of a acoustic dose meter 100 according to an embodiment of the present invention. Acoustic dose meter 100 is adapted as a unique acoustic sound generating and recording device. Acoustic dose meter 100 is adapted, in a preferred embodiment, to measure the volume density of pressurized medicine in a canister adapted for a MDI device on demand such as a canister referenced herein as canister 101. Acoustic dose meter 100 may be referred to hereinafter as a density or dose meter 100. Dose meter 100 may be provided in cylindrical form fabricated from a polymer rod and or tubing material. The cylindrical form is fabricated to produce a housing 103 for staging a canister and for securing electronic components thereof. Housing 103 may be open at the top portion thereof for the purpose of accepting MDI canister 101 therein for testing or metering. In one embodiment, housing 103 may be a solid rod of sufficient diameter and length that includes a central counter bore feature placed in one end of the cylinder, the feature of a diameter and depth sufficient for accepting an MDI canister 101 there within.

The counter bore feature has a depth sufficient to accept the full length of medicine canister 101 and an inside bore diameter that is larger than the outside diameter of canister 101. In this embodiment, a smaller diameter bore opening at the bottom and center of the counter bore feature accommodates the full length and diameter of a stem actuator 111 of MDI canister 101. Dose meter 100 includes a plurality of acoustic acoustic sound generators 102a arranged vertically and equally spaced in linear array. Acoustic generators 102a may be manufactured from a variety of disparate acoustic material such as quartz, ceramic, apatite, lead zirconate titanate, barium titanate, zinc oxide, aluminum nitride, lithium tantalate, potassium niobate, or other symmetric acoustic materials. Sound generators 102a may be embedded within the material of housing 103, attached to housing 103, or otherwise installed along one side of MDI canister 101. Acoustic generators 102a span the entire length of the MDI canister. Acoustic sound generators 102a are adapted to generate soundwaves that are directed toward a second vertical array of a same number of acoustic soundwave detectors 102b.

In one embodiment, acoustic generators 102a may be inset into the wall material on the inside of the counter bore material flush with or set just beyond the bore diameter so as not to restrict passage of the MDI canister into and out of the counter bore feature in dose meter 100. Acoustic soundwave detectors 102b may be disposed to and set within the wall material on the inside of the counter bore feature flush with or set just beyond the bore diameter and opposite of the acoustic sound generators 102a. Acoustic sound generators 102a may be activated on demand to generate soundwaves directed through MDI canister 101 resting within the counter bore seat on demand by using a switch 104 having an on and off setting that controls a Li ion battery 105 to deliver power each of sound generators 102a. Sound generators 102a may be connected in series in one embodiment or in parallel in another embodiment. The soundwaves generated are acoustic waves that penetrate MDI canister 101 and that are detected and recorded by acoustic sound detectors 102b on the opposite side of the canister.

Li ion battery 105 may be a rechargeable battery that may be charged using a micro universal serial bus (USB) port 109 adapted to receive a USB cable plugged into a USB port connected to a power source like a computer device or a wall outlet USB adapter. At least one light emitting diode (LED) 108 may be provided on housing 103 to indicate charge state of Li ion battery 105 to a patient. Switch 104 may control power to all acoustic sound generators 102a whereupon all sound generators 102a receive the appropriate power to produce the acoustic soundwaves at about the same instant. There are five sound generators 102a in this example however there may be more or fewer acoustic sound generators provided without departing from the spirit and scope of the present invention. In a preferred embodiment, the system is symmetrical in having the same number of sound generators and sound detectors arrayed at both sides of the MDI canister in the same vertical and linear spacing. In a preferred embodiment, sound generators 102a emit sound at a known radio frequency known to digital memory on dose meter 100.

Acoustic detectors 102b are adapted as acoustic soundwave detectors, each adapted to detect and record the frequency of the sound soundwaves sent by sound generators 102a after they have passed through MDI canister 101. Acoustic soundwave detectors 102b may be connected in series or parallel to a microprocessor 106. Microprocessor 106 may be mounted or otherwise contained within a hollowed compartment provided within housing 103 that may also house Li ion battery 105. An access door or panel 110 may be provided to enable access to the microprocessor and battery. Li ion battery 105 connects to microprocessor 106 and switch 104 may be used to boot microprocessor 106 when power is supplied to the acoustic components.

Microprocessor 106 may include memory containing machine instruction for calculating a mathematical relationship between acoustic sound frequency received at sound detectors 102b and the original sound frequency generated by sound generators 102a and then mathematically deduce the current volume density of the MDI canister 101 relative to an available number of metered doses that may be reserved in the MDI canister and actuated for delivery. If the canister is full then the difference between the frequency emitted and the soundwaves detected may be negligible and may indicate a "full canister" (maximum available metered doses).

In this embodiment, dose meter 100 includes a liquid crystal display (LCD) 107. LCD 107 is connected to microprocessor 106 and is adapted to display data such as device state information, device general information deemed important to a patient, and dose availability results relative to the current volume density of MDI canister 101 as determined in part by accounting for the deduced frequency variations (generated and detected average), the volume capacity of the MDI canister, and specific data defining metered dose volume or actuation dispense volume that may be stored on memory connected to or integrated with microprocessor 106. Microprocessor 106 may be aided by a software (SW) or firmware (FW) routine including the equations and steps for testing and calculating results.

Figure 1B:
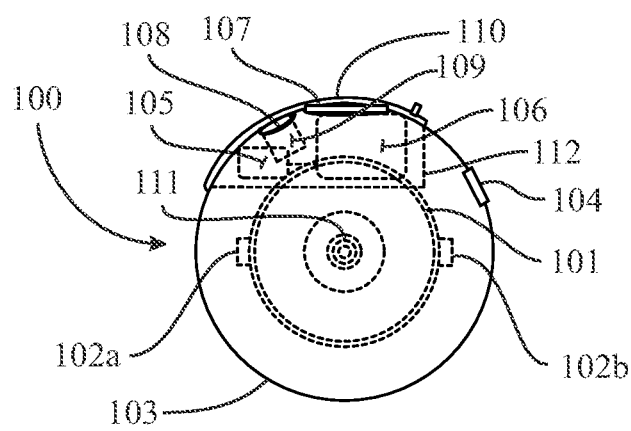
FIG. 1B is an end view of the acoustic dose meter of FIG. 1A.

FIG. 1B is an end view of acoustic dose meter 100 of FIG. 1A. In this end view, the annular and concentric properties of dose meter 100 are visible. MDI canister 101 fits inside the counter bore feature in concentric fashion, the extended bore seats actuator 111. In this view, acoustic sound generators 102a are disposed at center and directly across from or opposite of acoustic soundwave detectors 102b. In this view, microprocessor 106 and connected Li ion battery 105 are mounted or otherwise contained in a hollow compartment 112 and are accessible from the outside of dose meter 100 through door or panel 110. LCD display 107, LED 108, and micro USB port 109 are visible and or accessible from outside of housing 103. It is noted herein that passageways may be provided through the polymer material and are assumed present in this embodiment o enable power trace and or wire connections to be routed from microprocessor 106 to the other electronic components.

Figure 2:
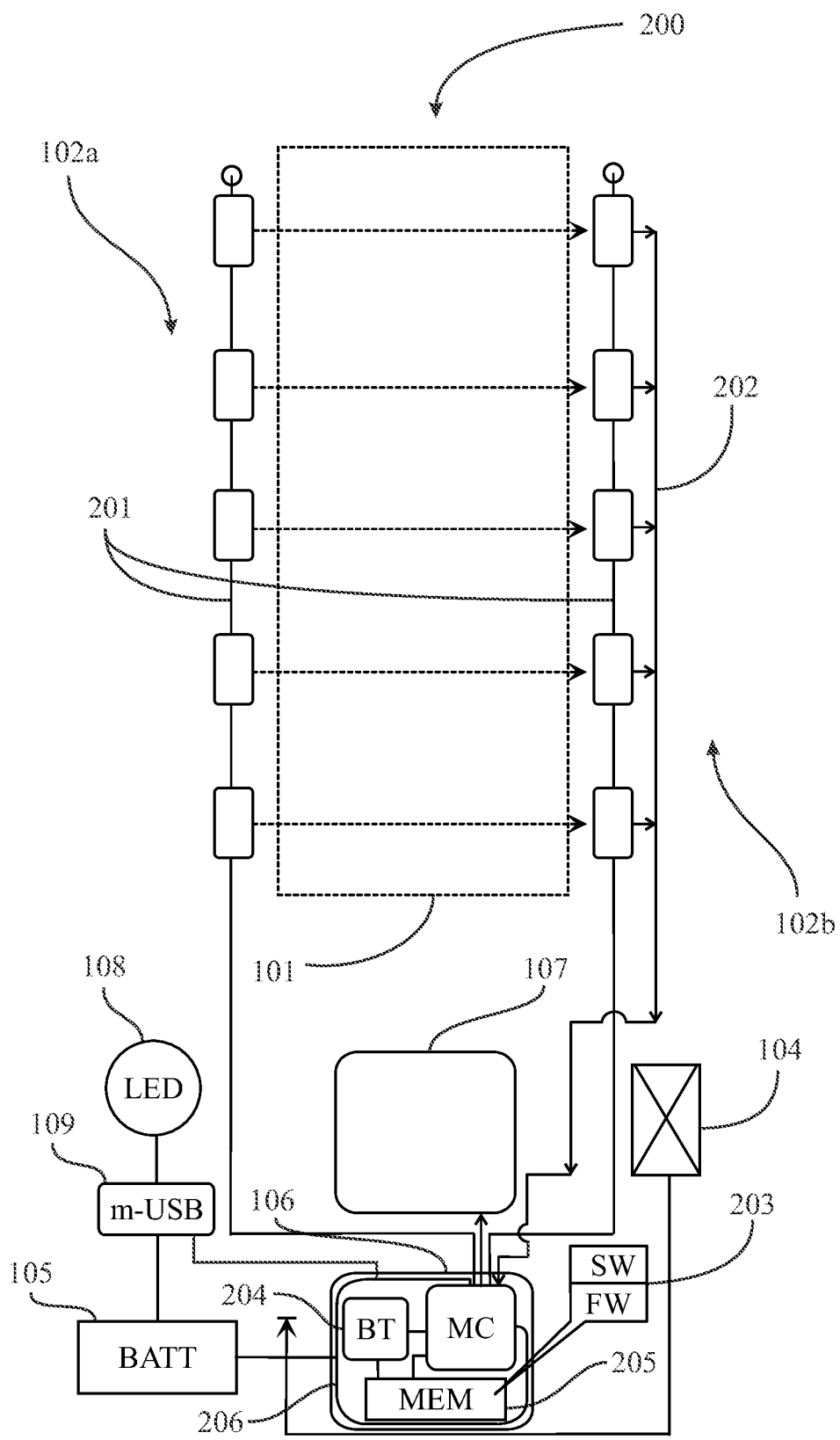
FIG. 2 is a block diagram depicting electrical connection of and interaction between components of the acoustic dose meter of FIG. 1A.

FIG. 2 is a block diagram 200 depicting electrical connection of and interaction between components of acoustic dose meter 100 of FIG. 1A. Diagram 200 is intended to logically represent placement and connection between components of dose meter 100 described above. Acoustic sound generators 102a align with acoustic soundwave detectors 102b on opposite sides of a footprint representing canister 101. Each acoustic array is serially connected electrically via electric traces or wires 201. Broken line directional arrows placed between sound generators 102a and soundwave detectors 102b represent generated acoustic soundwaves traveling through the MDI canister 101 and detected at each soundwave detector 102b.

In a preferred embodiment, detectors 102b record the frequency of the acoustic sound detected and pass the aggregate information onto a data line or trace to microprocessor 106. Microprocessor 106 may include a memory device (MEM) 205 integrated with or otherwise connected with the chip component (MC). MEM 205 may be adapted to perform, among other tasks, execution and run of a software or firmware machine instruction or machine code to evaluate and record received density data from the acoustic soundwave detectors 102b, average the values, and solving for the variance in average volume density compared to maximum volume density recorded in MEM as a constant. More calculation may be performed to determine a whole number representation of a number of metered doses that are still available in the MDI canister based on the density value of a single metered dose of the medicine contained within the canister.

In general use, a patient may insert an MDI medicine canister like canister 102 into the dose meter counter bore seat. The patient may switch on power to microprocessor 106 and to acoustic sound generators 102a. In one embodiment, microprocessor 106 is first booted before power is fed to acoustic components. In one embodiment, microprocessor 106 includes an external bus structure 206 for electrical support to micro USB port 109 and LED 108. In one embodiment, microprocessor 106 may be further enhanced with Bluetooth™ (BT) wireless communication via provision of a Bluetooth™ chip (BT) 204 connected or integrated with the processor and having connection or access to MEM 205. In one embodiment, microprocessor 106, memory 205, and BT™ chip 204 share a single printed circuit board (PCB).

Microprocessor 106 may be aided by FW or SW 203 to calculate density by volume using relational equations. An example of exemplary equations that may be used by SW/FW 203 and microprocessor 106 to calculate density may include use of a gas law law: $PV=nRT$ where $nR$ represents the mass characteristics of the substance and T is a temperature constant and V represents the volume capacity of the canister, also a constant. Density is equal to mass/volume and can be expressed as $nR/V$. Density is measured using the acoustic system acting as an acoustic density meter. When density is known, the equation then becomes $nR=density*volume$. Both density and volume become known, so microprocessor 106 enabled by SW/FW 203 may solve for $nR$. R may represent a constant and n may represent number of moles of a substance.

In general application, a patient may power up microprocessor 106 using switch 104, which causes automatic execution of SW/FW 203. The patient may enter data to be considered into memory accessible to microprocessor 106. A voltage may be applied to the acoustic system including sound generators 102a and soundwave detectors 102b. The patient may have a canister inserted for content measurement when dose meter 100 is powered on or may insert the canister at any time after the meter is powered on. After a canister is placed into the counter bored canister seat feature of dose meter 100, the acoustic system measures the current density of the pressurized canister and sends each measurement from each sensor 102b to microprocessor 106 aided by SW/FW 203. The calculations performed with the sensor data occur on microprocessor 106 automatically and a resulting value reflecting a number of metered doses available in the canister is presented in display 107. In one embodiment using Bluetooth™, dose meter 100 may also send a wireless notification to a Bluetooth™ enabled and wirelessly paired and connected computing appliance.

A metered dose is traditionally equated with one or more physical actuation events of a canister actuator like actuator 111. An MDI includes a button for actuating a dispense of a specific amount of aerosol content into a patient's lungs. A metered dose may be one actuation event. A metered dose may be two actuation events. A metered dose amount prescribed for a patient may be known to dose meter 100. Therefore, the data revealing the number of available doses left in any canister tested may be calculated specifically according to the patient's data. A patient requiring a heavier dose or a lighter dose will get a number reflective of those specific dose amounts.

Figure 3:
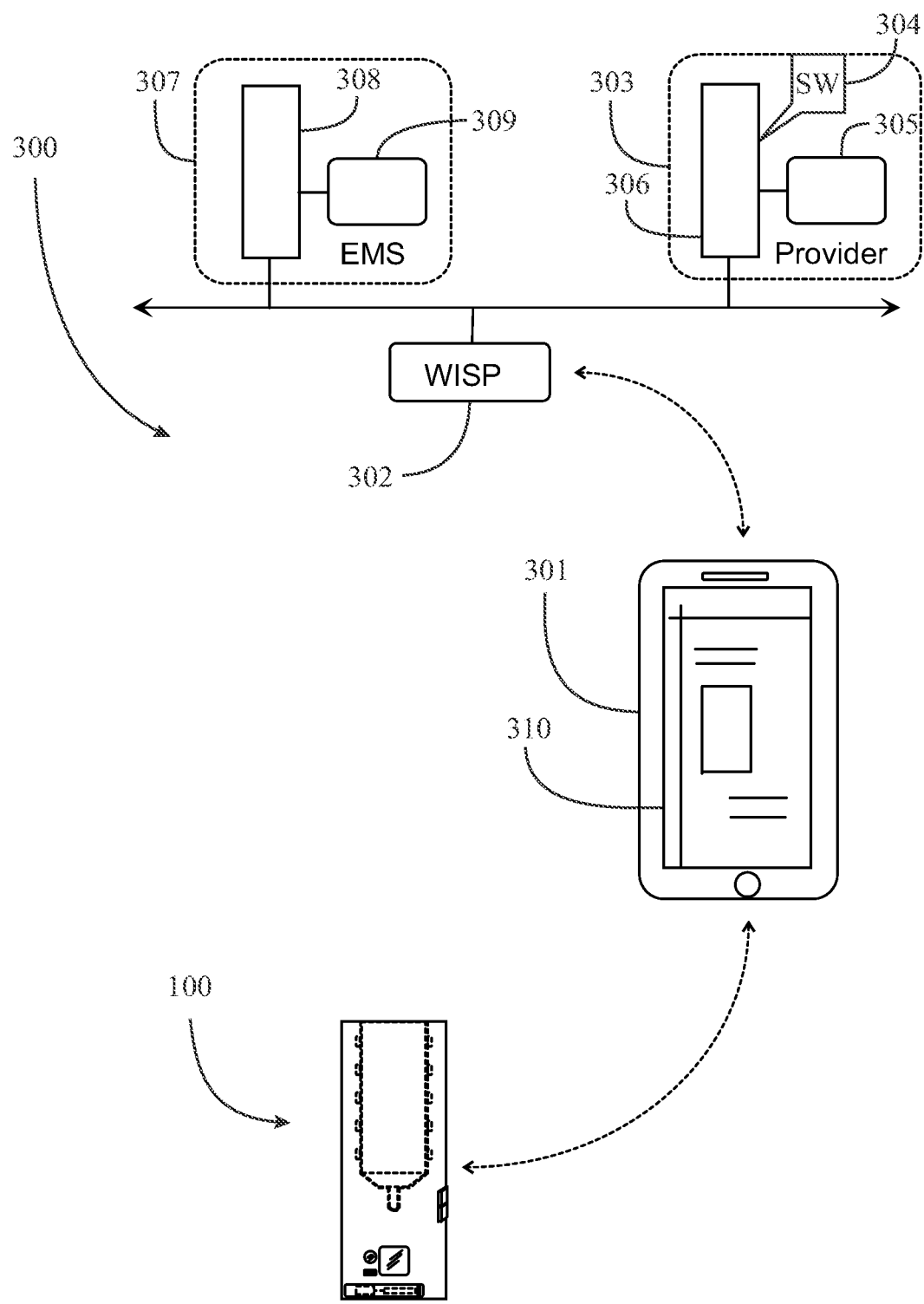
FIG. 3 is an architectural view of a network supporting network interaction between the acoustic dose meter of FIG. 1A and one or more network connected computing appliances.

FIG. 3 is an architectural view of a network 300 supporting network interaction between the acoustic dose meter of FIG. 1A and one or more network connected computing appliances. Network 300 may include dose meter 100 as a wireless peripheral device connected wirelessly by Bluetooth™ or another near field or local wireless network to a patient's mobile cell phone 301. Cell phone 301 may include a thin-client software application 310 adapted as a patient remote interface application to communicate or interact with acoustic dose meter 100. In one embodiment, information received at phone 301 maybe data synced or communicated to one or more other nodes on a larger information network such as the Internet network represented herein by a network backbone 311 accessible to patient phone 301 through a wireless Internet service provider (WISP) 302.

Network backbone 311 supports a service provider domain 303 that may be a medical provider site or portal frequented by a patient's physician including a pharmacy source where the patient may order MDI canisters containing the prescribed medicine. Typical nodes within domain 303 may include an information server 306 running a parent software (SW) application 304 and connected data repository 305 for storing the patient information including medical data. With respect to online domain 303, the patient may receive use statistics from dose meter 100 and forward those statistics to medical site domain 303 for medical evaluation and for medicine or prescription renewal or refill purposes. Changes in recommended dosage for a patient may be synced to the patient's application 310 and subsequently forwarded to dose meter 100 to replace the last dosage value entered, the new value used in subsequent calculations for determining available dosage remaining in a canister.

Network backbone 311 supports an emergency medical service (EMS) domain 307 that may be an emergency service portal operated locally to the patient such as a hospital service or paramedic service. In one application, a patient may discover that there are no viable doses left in a canister they originally perceived to have at least some medicine and may be in a compromised position with an oncoming COPD related event that may require hospitalization in absence of local medicine. Application 310 on patient phone 301 may send alert message calling for local services and additional patient information and location so emergency medical personnel may respond having accurate updated information about the patient usage of the medicine, dose amount, existing allergies, other known conditions, etc. Dose meter 100 enables a patient to clearly see dose availability left in any medicine canister without requiring manual effort on the part of the patient to keep track of a number of actuation events executed. The patient may quickly test through several canisters to determine those having dosage availability and those that are empty.

It will be apparent with skill in the art that the acoustic dosage meter of the present invention may be provided using some or all the elements described herein. The arrangement of elements and functionality thereof relative to the dosage meter of the invention is described in different embodiments each of which is an implementation of the present invention. While the uses and methods are described in enabling detail herein, it is to be noted that many alterations could be made in the details of the construction and the arrangement of the elements without departing from the spirit and scope of this invention. The present invention is limited only by the breadth of the claims below.

The invention claimed is:

1. An acoustic dose meter comprising:
a cylindrical housing including a cylindrical seat configured to stage a pressurized medicine canister having a first diameter, the housing having a length and a second diameter and including at least one compartment for housing electronics and passageways for connecting electronics for power and data communication;
a microprocessor including a transient memory containing machine instruction;
a power source connected to the microprocessor;
a power switch connected to the microprocessor and the power source for booting the microprocessor;
at least one visual display device connected to the microprocessor;
a first set of acoustic sensors positioned in a linear array along the length of the housing and connected to the microprocessor and adapted as acoustic sound generators; and
a second set of acoustic sensors positioned in a linear array along the length of the housing and configured to be positioned at an opposing position across the first diameter and are connected to the microprocessor and adapted as acoustic soundwave recorders;
wherein the housing length is greater than a length of the medicine canister and the microprocessor is configured to determine a volume density of medicine in the medicine canister and calculate an amount of remaining doses in the canister based on information received from the second set of acoustic recorders.

2. The acoustic dose meter of claim 1, wherein the power source is a rechargeable battery.

3. The acoustic dose meter of claim 2 further including a micro universal serial bus charging port connected to the microprocessor.

4. The acoustic dose meter of claim 3 further including a light emitting diode adapted to notify of a successful charge state of the battery.

5. The acoustic dose meter of claim 2, wherein the microprocessor and rechargeable battery are disposed within the at least one compartment and are accessible through a compartment door.

6. The acoustic dose meter of claim 1, wherein the cylindrical seat has a diameter larger than an outside diameter of the medicine canister and a length equal to or greater than a length of the medicine canister, and a centered bore disposed at a bottom of the cylindrical seat to accommodate an actuator of the medicine canister.

7. The acoustic dose meter of claim 6, wherein the cylindrical seat is a counter bored feature substantially centered in the housing.

8. The acoustic dose meter of claim 1, wherein the first and second sets of acoustic sensors are arrayed linearly and equally spaced apart, the first and second sets disposed on opposite sides of the cylindrical seat and aligned, the first set emitting soundwaves of a known first frequency, the second set detecting the soundwaves at a same or different second frequency.

9. The acoustic dose meter of claim 6, wherein the machine instructions include at least machine instruction for quantifying detected soundwave frequencies, differentiating the frequencies detected from the original first and second frequencies emitted, and deriving the amount of remaining doses based on the differences in frequencies and an original capacity of the medicine canister.

10. The acoustic dose meter of claim 1 further including a wireless communication chip connected to the microprocessor enabling data transfer from the acoustic dose meter to another wireless appliance.

11. The acoustic dose meter of claim 10, wherein the wireless communication chip is a Bluetooth™ communication chip.

12. The acoustic dose meter of claim 10, wherein the other wireless appliance in communication with the dose meter is a cellular phone running a thin client application adapted as a user interface to the acoustic dose meter.

13. The acoustic dose meter of claim 12, wherein the cellular phone has connection to a data network supporting at least one medical provider portal and at least one emergency services portal.

14. The acoustic dose meter of claim 12, wherein a wireless notification is configured to be communicated from the dose meter to the cellular phone, the notification including the amount of remaining doses for the medicine canister.

15. The acoustic dose meter of claim 1, wherein the second set of acoustic sensors communicate detected second frequency values to the microprocessor over a data line or trace.

16. The acoustic dose meter of claim 1, wherein the at least one visual display device is a liquid crystal display device controlled at the microprocessor.

17. The acoustic dose meter of claim 16, wherein the the amount of remaining doses is displayed on the liquid crystal display device.

18. The acoustic dose meter of claim 17, wherein the dose information displayed is the number of metered doses still available in the medicine canister.

19. The acoustic dose meter of claim 1, wherein the first and second sets of acoustic sensors are embedded into a housing material inside the cylindrical seat in a manner that does not obstruct an interior space of the cylindrical seat.

20. The acoustic dose meter of claim 1, wherein the medicine canister is one of a metered dose inhaler device.

* * * * *